United States Patent [19]

Prota et al.

[11] Patent Number: 5,374,288
[45] Date of Patent: Dec. 20, 1994

[54] OXIDATIVE HAIR DYEING METHOD, COMPOSITION, AND KIT UTILIZING HYDROXYL SUBSTITUTED BENZOTHIAZINES

[75] Inventors: Guiseppe Prota, Naples, Italy; Gottfried Wenke, Woodbridge, Conn.

[73] Assignee: Clairol Incorporated, Stamford, Conn.

[21] Appl. No.: 174,489

[22] Filed: Dec. 27, 1993

[51] Int. Cl.$^5$ ............................................... A61K 7/13
[52] U.S. Cl. ........................................... 8/406; 8/405; 8/407; 8/408; 8/409; 8/423; 8/565; 8/575
[58] Field of Search .............. 8/405, 406, 407, 408, 8/409, 423, 565, 575

[56] References Cited

U.S. PATENT DOCUMENTS

| | | | |
|---|---|---|---|
| 3,690,810 | 9/1972 | Bugaut et al. | 8/10.2 |
| 3,817,995 | 6/1974 | Bugaut et al. | 8/10 |

FOREIGN PATENT DOCUMENTS

| | | |
|---|---|---|
| 737265 | 2/1970 | Belgium . |
| 1245524 | 9/1971 | United Kingdom . |

*Primary Examiner*—Paul Lieberman
*Assistant Examiner*—Caroline L. Dusheck
*Attorney, Agent, or Firm*—Charles J. Zeller

[57] ABSTRACT

A process of dyeing hair by preparing and applying to the hair an aqueous reaction medium comprising dihydroxybenzothiazine and a periodsate, iodate, ferricyanide or persulfate oxidizing agent, the composition optionally containing a color modifier selected from the group consisting of direct dyes, primary intermediates, couplers, cysteine, dopa species and mixtures thereof, additionally containing a buffer to maintain the pH in the range from 2 to 11 during the oxidation reaction; and removing the aqueous reaction medium from the hair after the desired color is attained and compositions and kits for practicing such processes. The reaction medium may be formed by simultaneous addition of the benzothiazine and the oxidant to the hair or by addition of the benzothiazine followed addition of the oxidant.

12 Claims, No Drawings

OXIDATIVE HAIR DYEING METHOD, COMPOSITION, AND KIT UTILIZING HYDROXYL SUBSTITUTED BENZOTHIAZINES

FIELD OF THE INVENTION

This invention relates to compositions, methods and kits for dyeing hair. More specifically, the invention relates to methods of dyeing hair in which certain substituted 1,4-dihydrobenzothiazines are oxidized to produce phaeomelanins and trichochromes for coloring human hair. The invention relates also to compositions for conducting the hair dyeing process and to the packaged reactants sold in the form of a kit.

BACKGROUND OF THE INVENTION

Modern hair dyeing has developed from its initiation in the 1950's to the point where, today, it is the third largest product type in the hair category following shampoos and conditioners.

A wide variety of hair dyes or colorants have been developed, many of which involve oxidation of selected organic compounds or combinations of compounds with oxidizing agents such as hydrogen peroxide. Other known oxidizing agents for use with such compounds include perborates, persulfates, and perhalates, particularly periodates. These oxidizing agents are generally employed as ammonium salts or as salts of alkali metals. In the course of the development it has been learned that the applicability of an oxidant to one or more oxidizable substrates does not permit the prediction that the same oxidant or an apparently similar oxidant will be useful of oxidizing another oxidizable substrate to achieve a desirable color change in human hair.

Despite the large number of hair dyeing compositions and processes which have been developed, the art is constantly searching for methods and compositions to improve the efficiency of the hair coloring process, decrease the time required, impart desirable tints and tones to the hair and avoid the use of hydrogen peroxide, which may be damaging to the hair or to the skin which it contacts.

BRIEF SUMMARY OF THE INVENTION

It has now been found that an aqueous hair dyeing process utilizing selected hydroxy substituted 1,4-dihydrobenzothiazines at a pH of from about 2 to 11 can be practiced to achieve highly desirable permanent tints and tones in human hair.

Among the important advantages achieved by the practice of this invention, one of the most significant is that the oxidation is accomplished without the use of hydrogen peroxide, thereby avoiding the known disadvantages of this oxidizing agent. Another is that the oxidation of the substrates of the invention appears to follow a route which parallels human melanogenesis. The process is expected, therefore, to be toxicologically acceptable and to produce natural tones. Still another advantage is that at least some of the end products of the oxidation reaction are expected to be closely related to trichochromes or phaeomelanins the natural red and yellow pigments. Thus, by the practice of this invention it is possible to achieve natural appearing red and yellow hair tones which have heretofore eluded the art.

PRIOR ART

U.S. Pat. Nos. 3,690,810 and 3,817,995 describe hair coloring procedures in which hair is colored by oxidative coupling of certain preformed 5- or 7-hydroxybenzothiazines with conventional primary intermediates such as p-toluenediamine or 2,5-diamino-4-methyl anisole to produce hair coloring pigments which are oxidized prior to the coupling reaction. This hair coloring technique requires the use of 1,4-dihydrobenzothiazines. The only oxidative agent specifically mentioned and illustrated is hydrogen peroxide.

DESCRIPTION OF THE INVENTION

The hair dyeing process of the present invention, comprises the preparation of an aqueous hair dyeing composition containing selected hydroxy substituted 1,4-dihydrobenzothiazines and an inorganic oxidant in an aqueous medium at a pH of from about 2 to 11. The composition is then applied to the hair in such a manner that sufficient oxidation takes place, in the hair, to provide a tinctorially effective amount of hair coloring trichochrome or phaeomelanin or like pigment to permanently color the hair. The composition diffuses into the hair during the period of contact at a rate so that most of the pigment is formed in the hair and the hair is thereby permanently colored. The total contact time of the hair dyeing composition on the hair is normally less than one hour, typically from about 5 to 50 minutes, preferably 5 to 30 minutes.

By "permanent" is meant a color not removeable by shampooing with a conventional surfactant-containing shampoo, the permanency being attributable to the inability of the formed pigments to diffuse from the hair shaft in view of their molecular sizes.

By "applying" is meant contacting the hair to be dyed with a composition of the invention which is formed on the hair or just prior to contact with the hair, in a sufficient amount to effect a color change of the hair.

Trichochromes are polycyclic pigments generally characterized as yellow or red. Several of them are known and have been extracted from red hair and feathers under alkaline conditions.

Phaeomelanins are reddish-brown nitrogen and sulfur containing macromolecular pigments which are found in phaeomelanocytes. They are derived from tyrosinase oxidation of tyrosine and subsequent reaction with cysteine.

Tricochromes, phaeomelanins and like compounds are the end-product pigments of this invention. It is believed that these terms and their meanings are well understood by the skilled artisan even though the exact chemical identity of some of the products, particularly those formed by reaction of the intermediates formed during the oxidative process, with direct dyes, primary intermediates and/or couplers in accordance with the present invention is not precisely known or understood.

The dihydrobenzothiazines used in the practice of this invention may be represented by the formula:

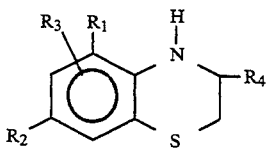

wherein $R_1$ and $R_2$ are hydrogen, $C_1$–$C_6$ alkyl or hydroxyl with the proviso that at least one of $R_1$ and $R_2$ must be hydroxyl; $R_3$ is hydrogen, $C_1$–$C_6$ alkyl, or hydroxyl; $R_4$ is H, $C_1$–$C_6$ alkyl $COOR_5$; and $R_5$ is H or $C_1$–$C_6$ alkyl The compounds are known or can be prepared by procedures known to those skilled in the art. See, for example, Ho et al, J. Medicinal Chem. 1981, Vol 24(6), 673–677; Prota et al, Gazz. Chim. Ital. 98, 495 (1968) and Prota et al, J. Heterocyclic Chem. 7, 555 (1970).

The compound 6-methyl-8-hydroxy-1,4-dihydrobenzothiazine, for example, is prepared by oxidation of 3,4-dihydroxytoluene with ferricyanide in the presence of 2-amino-ethyl thiol. Substitution of the aminoethanethio group at a position adjacent to the 4-hydroxyl group followed by spontaneous ring closure produces the desired compound.

The reaction of 2-amino-ethyl thiol with benzoquinone followed by air oxidation affords 6-hydroxy-dihydro-1,4-benzothiazine.

2-Carboxy-6-hydroxy-dihydro-1,4-benzothiazine is prepared by substitution of a cysteinyl moiety on benzoquinone followed by periodate oxidation to form the corresponding 2H-1,4-benzothiazine which is then reduced to form the desired compound.

The amount of substituted dihydrobenzothiazine which will be tinctorially effective depends upon many factors which can be readily evaluated by the skilled artisan either from experience or from a few simple tests. These factors include, for example, the color desired, the selected coloring agent or agents, the original color of the hair to be treated, the pH, auxiliary coloring agents employed, etc. Typically, however, the compositions of the invention will contain from about 0.1 to 10% percent by weight colorant i.e. hydroxy substituted dihydrobenzothiazine preferably 0.1 to 2 percent.

All percents by weight defined in this specification and claims are percents by weight based on the total weight of the composition.

The oxidizing agents employed in this invention may be selected from, periodate, iodate, persulfate and ferricyanide oxidizing agents including ammonium salts and salts of alkali metals, preferably sodium or potassium. The presently preferred oxidizing agent is sodium periodate. Sodium salts are preferred because they are readily available and easily soluble in water.

The selected oxidant will be employed in amounts sufficient to produce useful quantities of hair colorants. Typically this will vary from an approximate stoichoimetric equivalent to a reasonable excess. The amount is not critical and will, of course, depend upon the oxidant selected.

Inasmuch as the pH of the reaction medium will vary during the reaction, it is desirable to provide a sufficient amount of a pH control agent in the reaction medium to maintain the requisite pH. In the process of the present invention, the preferable pH depends on the oxidant selected and on the dyeing procedure (one-step dyeing or two-step dyeing). Persulfates are usually optimal at an alkaline pH, while periodates and iodates can be used at a broad pH-range (pH 2–11). With periodate oxidant, the preferred pH range is pH 5–8. Ferricyanide is used at a pH 6–11, preferably 7–9.

Reagents for the control of pH in the compositions of this invention include various conventional buffers including those based on inorganic salts such as carbonates and bicarbonates. The pH control agents also include organic compounds widely employed in hair colorant compositions to maintain the desired pH. These include, for example, fatty acids especially long chain monocarboxylic or dicarboxylic acids such as dimer acid, linoleic acid or stearic acid in combination with amines such as ammonia, 2-amino-2-methyl propanol and monoethanol amine. Both types of reagents are referred to herein, and in the appended claims as pH control agents.

In the hair dyeing process of this invention, the selected substituted benzothiazine is applied to the hair in an aqueous composition at the selected pH in the presence of the selected oxidizing agent and maintained in contact with the hair for a sufficient period of time for a tinctorially effective amount of pigment to form. As aforesaid, most of the tinctorially effective pigment should form in the hair so that it elicits a permanent color change. It is believed that the substituted dihydroxybenzothiazine molecule is sufficiently small so that it will migrate into the hair strand along with the oxidizing agent and the aqueous carrier. The trichochromes, phaeomelamins and like pigments that form, however, are such large molecules that they become trapped within the hair strand, thereby imparting the permanent color. It will be apparent that applying the hair dye composition to the hair after an appreciable amount of oxidation has taken place is not suitable since the pigments will not diffuse into the hair, and will be largely stripped away during subsequent shampooing.

The "contact time" as that term is employed herein is the period of time from the mixing of the reactants to the removal from the hair.

There are a number of variations in the procedure of this invention which can be employed to achieve the desired results. These include, for example, the one and the two step processes and the post-oxidative process.

In the one step or simultaneous procedure, the mixture of hair colorant and oxidizing agent in aqueous medium at the selected pH are maintained in contact until sufficient oxidation products are formed to effect the desired result. The hair is then rinsed and dried.

In the two step or sequential process, the colorant in an aqueous medium at the selected pH, is applied to the hair and left for a period of from about 1 to 30 minutes preferably 10 to 20 minutes. A dilute aqueous solution of the oxidant is then brought into contact with the hair for another 1 to 20 minutes preferably 2 to 10 minutes until the desired coloration is attained. The hair is then rinsed and dried.

The post-oxidative procedure is employed when a high degree of coloring is desired. It may be used following the one step process. The preferred oxidant is sodium periodate, but other oxidants may be employed. The essence of the procedure is that, after application of the one step process, the hair, preferably after rinsing is again treated with an oxidant. The purpose of the post-oxidation treatment is to complete the conversion to useful pigment of any pigment precursor which may have migrated into the hair strand during the initial treatment but was not converted to a permanent coloring pigment.

The exact mechanism by which the hydroxy substituted benzothiazines of this invention are converted to useful pigments is not known.

A further aspect of the present invention is the optional incorporation of a hair color modifier selected from the group consisting of one or more direct dyes, primary intermediates, couplers, cysteine and mixtures thereof in the oxidation mixture. Preferred modifiers include dihydroxyphenylalanine (DOPA) and other dopa species, especially if the oxidizing agent is ferricyanide. It is believed that these components, when present, react at least in part with the intermediate compounds formed during pigment production thereby providing additional chromatic characteristics to the pigments ultimately obtained. When such color modifiers are employed, the amount of oxidant in the reaction mixture is increased to provide for the oxidation of these materials since some of them will be directly oxidized in the usual way rather than reacting with an intermediate of the primary reaction sequence. It will be apparent to the skilled artisan that by use of these auxiliary coloring agents, a wide variety tints, tones and shades can be achieved.

The term "dopa species" includes dopa itself as well as homologs, analogs and derivatives of DOPA. It includes, for example cysteinyl dopa, alpha alkyl dopa having 1 to 4, preferably 1 to 2 carbon atoms in the alkyl group, epinephrine and dopa alkyl esters having 1 to 6, preferably 1 to 2 carbon atoms in the alkyl group.

The concentration of hair color modifier is normally less than about 10 mg/ml, and preferably is present in the reaction medium at from about 0.01 to about 5 mg/ml, most preferably from about 0.05 to about 2 mg/ml. The amount of these components should not be so great as to prevent the formation of the principal pigment. That is, the process of the present invention contemplates reaction of only a portion of the intermediate reaction products with the hair color modifiers.

A wide variety of direct dyes, primary intermediates and couplers are known to the skilled artisan and can be employed in this invention.

The presently preferred primary intermediates and couplers include:
Primary p-phenylenediamine
Intermediates:
  p-aminophenol
  o-aminophenol
  N,N-bis(2-hydroxyethyl)-p-phenylenediamine
  2,5-diaminopyridine
  p-toluenediamine
Couplers:
  resorcinol
  m-aminophenol
  α-naphthol
  5-amino-o-cresol
  2-methylresorcinol
  N-acetyl dopa
  4,6-di(hydroxyethoxy)-m-phenylenediamine
  m-phenylenediamine Suitable direct dyes include, for example nitro dyes, azo dyes and anthraquinone dyes.

Another optional modifier which can be employed in the process of this invention is the amino acid cysteine. It is used at substantially the same concentration as other modifiers to achieve desirable hair colors. The exact mechanism by which cysteine operates is not known. It probably substitutes on the benzene ring through a thio group.

It will be understood that the pigments formed in accordance with this invention are totally different from those formed in accordance with the procedures of U.S. Pat. No. 3,690,810 and 3,817,995 identified above. In these patents, the procedure is one in which the selected 5- or 7-dihydroxybenzothinzene is coupled with a primary intermediate and the coupled product oxidized. In the process of this invention, when a color modifier such as a coupler or a primary intermediate is employed, the selected hydroxy substituted benzothiazine is oxidized and the products formed (intermediates or phaeomelanin precursors) react with the color modifier to form a trichochrome or phaeomelanine like pigment.

The variously described embodiments of the present invention may also include in the hair dye composition one or more optional ingredients, which may be provided in one or more additional containers of the kits to be described in more detail hereinafter for admixture by the user into the aqueous reaction mixture, or, if compatible, may be incorporated into the oxidant or colorant premix solutions described previously.

Such ingredients include well known conventional additives usually employed in oxidative hair coloring compositions such as organic solvents, thickeners, surface-active agents, pH adjusting agents, antioxidants, fragrances and chelating agents.

The hair dye compositions used in the process of the present invention can include an organic solvent as a cosolvent. The organic solvent may assist in the dissolution of the components of the composition, and is present typically in an amount up to about 30%, preferably up to about 15%. A desirable range is from about 0.1 to about 15%, most preferably from about 1 to 10%. Suitable solvents are mono- and polyhydric alcohols, for example, ethyl alcohol, isopropyl alcohol, propylene glycol, benzyl alcohol, etc., and glycol ethers, such as 2-butoxyethanol, ethylene glycol monoethyl ether and diethyleneglycol monoethyl ether.

Surface-active agents employed in the dyeing compositions of this invention can be anionic, nonionic, cationic, amphoteric or zwitterionic. By way of examples of the various types of surface-active agents, there can be mentioned: higher alkylbenzene sulfonates; alkylnaphthalenesulfonates; sulfonated esters of alcohols and polybasic acids; taurates; fatty alcohol sulfates; sulfates of branched chain or secondary alcohols; alkyldimethylbenzylammonium chlorides, salts of fatty acids or fatty acid mixtures; N-oxyalkylated fatty acid alkanolamides, and the like. Illustrative of specific surfactants there can be mentioned: sodium lauryl sulfate; polyoxyethylene lauryl ester, myristyl sulfate; glyceryl monostearate; triethanolamine oleate, sodium salt of palmitic methyl taurine; cetyl pyridinium chloride; lauryl sulfonate; myristyl sulfonate, lauric diethanolamide; polyoxyethylene stearate; ethoxylated oleoyl diethanolamide; polyethylene glycol amides of hydrogenated tallow; stearyldimethyl benzyl ammonium chloride; dodecylbenzene sodium sulfonate; triethanolamine salt of p-dodecylbenzene sulfonate; nonylaphthalene sodium sulfonate; dioctyl sodium sulfonsuccinate; sodium N-methyl-N-oleoyl taurate; oleic acid ester of sodium isothionate; sodium dodecyl sulfate; the sodium salt of 3-diethyl tridecanol-6-sulfate and the like. The quantity of surface-active agent can vary over a wide range, such as from about 0.05% to 15% and preferably from about 0.10 to 5% by weight of the composition. The anionic and nonionic surfactants are employed typically as emulsifiers, while the cationic surfactants are useful to impart a hair conditioning benefit to the hair. Care must be exercised when anionic and cationic surfactants are both incorporated, in view of possible incompatibility.

Chelating and sequestering agents include, for example, ethylenediaminetetraacetic acid, sodium citrate, etc., and if used, may be present in an amount of under about 1%.

A thickening agent may also be incorporated in the dyeing composition of this invention, which may be one or several of those commonly used in hair dyeing. These are exemplified by such products as sodium alginate or gum arabic, or cellulose derivatives, such as methylcellulose, e.g., Methocel 60HG, or the sodium salt of carboxymethylcellulose, or hydroxyethyl-cellulose, e.g., Cellosize QP-40 or acrylic polymers, such as polyacrylic acid sodium salt, or inorganic thickeners, such as bentonite. The quantity of this thickening agent can also vary over a wide range, even as high as 20%. Ordinarily it will range from about 0.1 to 5% by weight of the composition. The viscosity of the composition may vary from about 1 cp to about 100,00 cps. For a typical lotion formulation, composition viscosity is between about 100 cps to about 10,000 cps, at which viscosity the composition can be applied to the hair without running or dripping.

The list of optional ingredients is not intended as limiting. Other suitable adjuvants for inclusion in the hair dye composition are recited, for example, in Zviak, *The Science of Hair Care* (1986) and Balsam and Sagarin, *Cosmetics: Science and Technology*, Vol. 2 (Second Edition 1972).

The process of the present invention may conveniently be practiced by providing premeasured amounts of the reactants in separate containers packaged in kit form. The user simply admixes the reactants for application to the hair in accordance with the selected practice of the invention. It will be apparent that no special expertise is required to carry out the process, and accordingly the product and process are equally suitable for in-home use by the nonprofessional as well as salon use by the professional. Advantageously, the product in kit form is shelf-stable and is therefore suitable for retail sale without precautions required for some hair clorant compositions, e.g., storage under anaerobic conditions.

The kit provided in accordance with this aspect of the invention comprises a first container containing the oxidizable colorant and a second container containing the oxidant in an aqueous solution. The buffer may be individually packaged in a third container, or it may be present in the first or second container. Selected modifiers may be mixed with the basic hair colorant of the invention or may be in separate containers.

While the kit may include packets containing amounts, preferably premeasured, of dry powders for preparation of these solutions, it is more convenient to provide them as solutions. Moreover, solutions containing premeasured quantities of the constituents facilitates their correct use by the consumer.

One or more additional containers containing the optional constituents may be provided in the kit. The optional constituents may also be contained within the solutions of the previously described containers, barring any incompatibility.

The consumer admixes the components of the kit, suitably as the aqueous solutions or as dry powders and water, according to written instructions, to obtain the aqueous reaction mixture. Mixing may be conducted in a separate vessel supplied with or external to the kit, or may take place in a container of the kit adapted to provide sufficient head space for mixing. The reactants may also be admixed on the hair of the user. Reaction commences upon mixing. The hair colorant will subsequently oxidize as described herein whereby a permanent hair color is obtained. After the desired hair shade is reached, most preferably within about 30 minutes, the hair dye composition that was applied to the hair is removed, preferably with a conventional shampoo.

The hair coloring effects achieved with the process of this invention may be evaluated utilizing the standard Hunter Tristimulus values. In the Hunter method, the parameters a and b may be positive or negative and define the chromatic condition of the hair. Thus, the more positive the value, the greater the redness of the hair, while a negative a value indicates greenness., Similarly, positive b values indicate yellowness, while negative b values indicate blueness. The L parameter is a measure of color intensity, and has a value of 0 for absolute black to 100 for absolute white. Generally, hair having an L value of about 15 or less is considered black, while an L value of about 60 is white. It should be understood that the L value scale is not linear, but rather is sigmoidal. Proximate to 0 and proximate to 100 hair color intensity apparent to the human eye varies minimally with unit changes in the L value. Between values of about 20 to about 50, hair color intensity varies significantly with unit changes in L value. Thus, the Hunter values are more sensitive in the region where the human eye is able to perceive color changes.

The following non-limiting examples are given by way of illustration only.

EXAMPLE 1

20 mg 8-hydroxy-1,4-dihydrobenzothiazine and 8 mg sodium bicarbonate were dissolved in 1 ml diethyleneglycolmonoethylether and 4 ml water. The pH of the solution was approximately 7.0. White hair was exposed to the solution for 10 minutes. The hair was rinsed with water before being exposed to a 2% aqueous solution of sodium periodate for 2 minutes. The hair was rinsed with water and dried with a hair-dryer. The hair had a golden blonde color.

|  | L | a | b |
|---|---|---|---|
| Hunter Tr. val. before dyeing: | 67.1 | −0.6 | 18.5 |
| Hunter Tr. val. after dyeing: | 40.0 | 5.5 | 15.1 |

EXAMPLE 2

20 mg 8-hydroxy-1,4-dihydrobenzothiazine and 8 mg sodium bicarbonate were dissolved in 1 ml diethyleneglycolmonoethylether and 4 ml water. The pH of the solution was approximately 7.0. White hair was exposed to the solution for 10 minutes. The hair was rinsed with water before being exposed to a 2% aqueous solution of sodium iodate (pH adjusted to 4.2 with citric acid) for 2 minutes. The hair was rinsed with water and dried with a hair-dryer. The hair had an ash blonde color.

|  | L | a | b |
|---|---|---|---|
| Hunter Tr. val. before dyeing: | 67.1 | −0.6 | 18.5 |
| Hunter Tr. val. after dyeing: | 42.5 | 2.3 | 10.7 |

EXAMPLE 3

20 mg 6-hydroxy-1,4-dihydrobenzothiazine and 36 mg sodium iodate were dissolved in 1 ml diethyleneglycol-monoethylether and 4 ml water. The pH of the solution was approximately 5. White hair was exposed to the solution for 10 minutes. The hair was rinsed with water and dried with a hair-dryer. The color of the hair was violet-brown.

|  | L | a | b |
|---|---|---|---|
| Hunter Tr. val. before dyeing: | 67.1 | −0.6 | 18.5 |
| Hunter Tr. val. after dyeing: | 24.3 | 4.7 | 1.3 |

EXAMPLE 4

White hair was exposed to the hair dyeing solution of example 3 for 10 minutes. After rinsing with water, the hair was exposed to a 2% aqueous solution of sodium periodate for 2 minutes. The hair was rinsed with water and dried with a hair dryer. The color of the hair was dark gray-violet.

|  | L | a | b |
|---|---|---|---|
| Hunter Tr. val. before dyeing: | 67.1 | −0.6 | 18.5 |
| Hunter Tr. val. after dyeing: | 20.7 | 3.5 | 0.0 |

EXAMPLE 5

20 mg 2-carboxy-6-hydroxy-1,4-dihydrobenzothiazine, 8 mg sodium bicarbonate and 36 mg sodium iodate were dissolved in 2 ml methanol and 3 ml water. The pH of the solution was approximately 7.2. White hair was exposed to the solution for 10 minutes, rinsed with water and dried. The hair was dyed to a reddish-brown color.

|  | L | a | b |
|---|---|---|---|
| Hunter Tr. val. before dyeing: | 67.1 | −0.6 | 18.5 |
| Hunter Tr. val. after dyeing: | 41.5 | 7.0 | 14.8 |

EXAMPLE 6

50 mg 6-hydroxy-1,4-dihydrobenzothiazine was dissolved in 2 ml methanol and 3 ml water. The pH of the solution was adjusted to 10.0 by addition of sodium carbonate. White hair was exposed to this solution for 20 minutes. The hair was rinsed with water and treated with a 1% aqueous solution of sodium periodate for 5 minutes. The hair was rinsed with water and dried. The hair was dyed to a dark brown color.

|  | L | a | b |
|---|---|---|---|
| Hunter Tr. val. before dyeing: | 67.1 | −0.6 | 18.5 |
| Hunter Tr. val. after dyeing: | 19.9 | 1.4 | 2.8 |

EXAMPLE 7

Gray hair was treated as described in example 6. The hair was dyed to a medium brown color.

|  | L | a | b |
|---|---|---|---|
| Hunter Tr. val. before dyeing: | 36.0 | 0.6 | 5.2 |
| Hunter Tr. val. after dyeing: | 25.3 | 1.1 | 3.9 |

What is claimed is:

1. A method permanently coloring hair which comprises applying to the hair an aqueous oxidizing composition at a pH of from about 2 to 11 and comprising a tinctorially effective amount of a hair colorant compound represented by the formula:

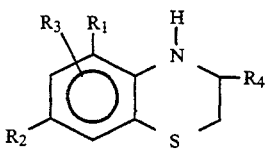

wherein $R_1$ and $R_2$ are hydrogen, $C_1$-$C_6$ alkyl or hydroxyl with the proviso that at least one of $R_1$ and $R_2$ must be hydroxyl; $R_3$ is hydrogen, $C_1$-$C_6$ alkyl, or hydroxyl; $R_4$ is H, $C_1$-$C_6$ alkyl or $COOR_5$; and $R_5$ is H or $C_1$-$C_6$ alkyl, together with a periodate, iodate, ferricyanide or persulfate oxidizing agent and permanently coloring the hair by allowing the composition to remain on the hair to achieve the desired color by the formation of phaeomelanin, trichochrome or closely related pigments thereof in the hair.

2. The method of claim 1 wherein the composition additionally contains a color modifier selected from the group consisting of direct dyes, primary intermediates, couplers, cysteine, dopa species and mixtures thereof.

3. The method of claim 1 wherein the oxidizing composition is formed on the hair by sequential addition of the hair colorant compound and the oxidizing agent.

4. The method of claim 1 wherein the oxidizing composition is formed on the hair by simultaneous addition of the hair colorant compound and the oxidizing agent.

5. The method of claim 4 additionally including a post-oxidative step with an oxidizing agent.

6. The method of claim 2 wherein the dopa species is dopa.

7. An aqueous composition for permanently dyeing hair comprising a hair colorant compound and an oxidizing agent selected from the group consisting of periodate, iodate, ferricyanide and persulfate oxidizing agent, which is tinctorially effective to permanently color the human hair; said hair colorant compound being represented by the formula:

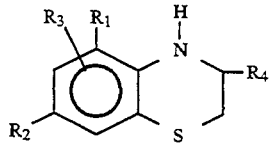

wherein $R_1$ and $R_2$ are hydrogen, $C_1$-$C_6$ alkyl or hydroxyl with the proviso that at least one of $R_1$ and $R_2$ must be hydroxyl; $R_3$ is hydrogen, $C_1$-$C_6$ alkyl, or hydroxyl; $R_4$ is H, $C_1$-$C_6$ alkyl $COOR_5$; and $R_5$ is H or $C_1$-$C_6$ alkyl.

8. The composition of claim 7 additionally containing a color modifier selected from the group consisting of direct dyes, primary intermediates, couplers, cysteine, dopa species and mixtures thereof.

9. The composition of claim 7 or 8 wherein the dopa species is dopa.

10. A hair dyeing kit for permanently dyeing human hair which includes in a single package a plurality of containers comprising (a) a first container containing including a hair colorant represented by the formula:

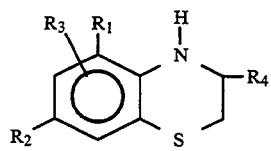

wherein $R_1$ and $R_2$ are hydrogen, $C_1$–$C_6$ alkyl or hydroxyl with the proviso that at least one of $R_1$ and $R_2$ must be hydroxyl; $R_3$ is hydrogen, $C_1$–$C_6$ alkyl, or hydroxyl; $R_4$ is H, $C_1$–$C_6$ $COOR_5$; and $R_5$ is H or $C_1$–$C_6$ alkyl and (b) a second container containing a periodate, iodate, ferricyanide or persulfate oxidizing agent; and in one of said containers or a separate container a pH control agent, the amount of said agent contained in the kit being sufficient to provide a pH of from about 2 to 11 when the contents of the containers are mixed, the amount of hair colorant and oxidant in the kit being sufficient to effect such permanent dyeing of hair when the contents of the containers are mixed and applied to the hair.

11. The hair dyeing kit of claim 10 additionally containing in the first or a separate container, other than the container containing the oxidizing agent, a color modifier selected from the group consisting of direct dyes, primary intermediates, couplers, cysteine, dopa species and mixtures thereof.

12. The hair dyeing kit of claim 10 or 11 wherein the dopa species is dopa.

* * * * *